United States Patent [19]
Den Ouden et al.

[11] Patent Number: 5,496,327
[45] Date of Patent: Mar. 5, 1996

[54] APPARATUS FOR INSERTING PINS IN OSSEOUS MATERIAL

[76] Inventors: Arie H. Den Ouden, Goudkruid 46, NL-3068 SZ Rotterdam, Netherlands; Dirk B. Van Egmond, Utrechtsestraatweg 36, NL-3445 AS Woerden, Netherlands

[21] Appl. No.: 149,118

[22] Filed: Nov. 9, 1993

[30] Foreign Application Priority Data

Nov. 9, 1992 [NL] Netherlands ............................ 9201959

[51] Int. Cl.⁶ .................................................. A61B 17/18
[52] U.S. Cl. .......................... 606/104; 606/103; 606/98
[58] Field of Search ...................................... 606/103, 104, 606/99, 98, 84, 169; 173/129, 163

[56] References Cited

U.S. PATENT DOCUMENTS

| | | | |
|---|---|---|---|
| 3,975,032 | 8/1976 | Bent | 606/104 X |
| 4,109,735 | 8/1978 | Bent | 606/104 X |
| 4,140,111 | 2/1979 | Morrell | 606/104 |
| 4,275,893 | 6/1981 | Bilanceri | 606/104 X |
| 4,298,074 | 11/1981 | Mattchen | 606/104 |
| 4,441,563 | 4/1984 | Walton, II | 606/104 X |
| 4,549,538 | 10/1985 | Schadrack, III et al. | 606/104 |

*Primary Examiner*—Stephen C. Pellegrino
*Assistant Examiner*—Michael Peffley
*Attorney, Agent, or Firm*—Young & Thompson

[57] ABSTRACT

Apparatus for inserting pins in osseous material by vibration. The apparatus has a fixed housing with a cavity for moving the pins therethrough. At the proximal end the housing has a clamping device which operates in one direction. Vibration means inside the housing impose vibrations on the pin to insert them into the osseous material.

7 Claims, 2 Drawing Sheets

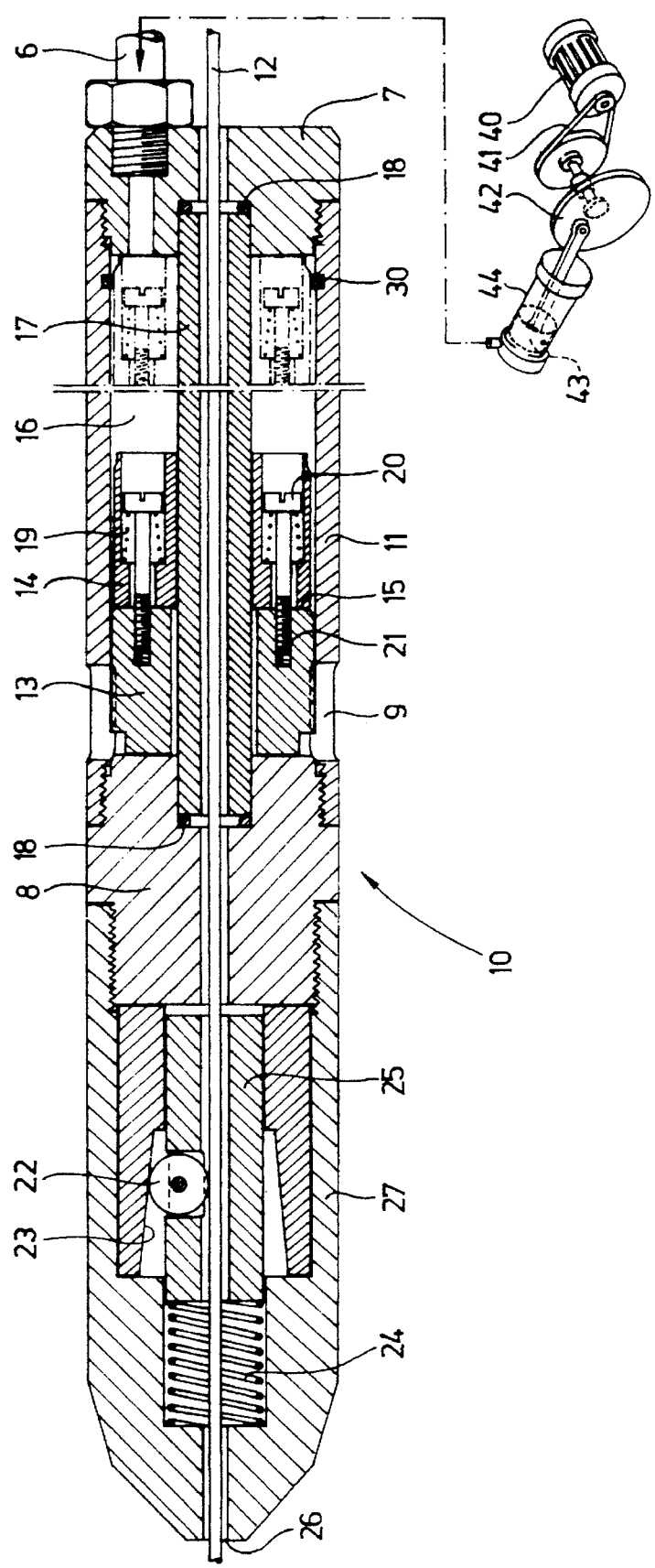

5,496,327

APPARATUS FOR INSERTING PINS IN OSSEOUS MATERIAL

FIELD OF THE INVENTION

The present invention relates to an apparatus according to an apparatus for inserting pins in osseous material by means of vibration, comprising a proximal outer section located in the vicinity of the bone material during use and a distal section which is remote from the bone material during use of the apparatus, the proximal section being provided with clamping means for the pins and being arranged to allow free transport of the wire An the proximal-dietal direction, vibration means for the pin being present between the proximal section and the distal section and the apparatus being provided with e receiver for the pin.

BACKGROUND OF THE INVENTION

Vibration apparatuses are used, for example, for inserting so-called "Kirschner" wires, which are termed "pins" below. Such pins are used in surgery, in particular in the case of broken bones. The use of such pins has The advantage that said pins are easy and quick to insert and that soft tissue present is damaged to a lesser extent than is the case with other techniques. After healing, the pins can be removed easily. In the prior art pins of this type are inserted in the bones with the aid of e rotary drive device. With this procedure the front end of the pins is provided with a ("Trocart") tip and said pins serve simultaneously as drill and as internal splint.

U.S. patent specification 4,298,074 discloses such a vibration apparatus. In this patent a percussion apparatus is shown where the wire is introduced into the apparatus from the proximal end. By moving the clamping head for the wire in the vicinity of the proximal end relative to the housing of the apparatus, provision can be made for unlocking the clamping means for introduction of the wire. This apparatus has the disadvantage that a clamping head of this type of design is relatively complex and has an associated risk of incorrect operation. Moreover, the length of the wires which can be inserted using such an apparatus is limited. After all, it is extremely important that the free end of the clamping means is located as close as possible to the bone into which the w wire is inserted.

The object of the present invention is to simplify the apparatus described above, in respect of both design and operation, and to make it possible to insert wires of greater length.

SUMMARY OF THE INVENTION

According to the invention an apparatus for inserting pans in osseous material by means of vibration, comprising a proximal outer section located in the vicinity of the bone material during use and a distal section which is remote from the bone material during use of the apparatus, the proximal section being provided with clamping means for the pins and being arranged to allow free transport of the wire in the proximal-distal direction, vibration means for the pin being present between the proximal section and the distal section end the apparatus being provided with a receiver for the pin, wherein the distal and the proximal sections are connected to one another and immobile with respect to one another, wherein the accommodation for the pin comprises a cavity extending through the entire apparatus and wherein the clamping means are arranged to allow free transport of the wire in the proximal-distal direction only.

With the apparatus now proposed the clamping means have to function in one direction only. Pins of unrestricted length can be inserted. Because the clamping means now no longer have to be fitted so that they are movable relative to the housing, the design of the apparatus can be appreciably simplified.

In order to control the pins, the apparatus can first be positioned with a specific orientation with respect to the relevant part of the body. Furthermore, it is possible to vary both the vibration frequency and the energy introduced. This can be effected, for example, by changing the amplitude of the vibration or stroke. Although the invention has been described above with reference to the use of so-called "K wires", it must be understood that it is also possible to insert thicker or thinner pins, or pans of a different using this kind of vibrations or strokes. The vibration or percussion means can comprise all vibration means disclosed in the prior art, such as electrical or mechanical means. In this context particular preference is given to pneumatic vibration means. A differentiation must be made between vibration means of this type and percussion means, such as are disclosed, for example, in the prior art. The stroke or vibration frequency is preferably above 5 Hz. It will be obvious that such a frequency can not be generated in the case of a manually operated apparatus. According to a further advantageous embodiment, the apparatus comprises a reciprocating percussion or vibration body which strikes against a stop. In order, on the one hand, to guarantee that the bone is drilled through but, on the other hand, to prevent splintering occurring during drilling, the mass of such a percussion or vibration body must be below 50 gram and preferably about 20 gram.

According to an advantageous embodiment of the invention, the reciprocating percussion or vibration body comprises a hollow piston assembly. Said piston assembly must be hollow in order to receive a guide tube for the wire to be inserted. The piston assembly preferably comprises two piston sections, one piston section providing a seal with respect to the tube surrounding the piston, whilst the other piston section provides a seal with respect to the guide tube incorporated therein. Said piston sections must be movable in a sealing manner relative to one another in a radial direction. Pin transport can be effected in any manner disclosed in the prior art, only forward movement of the pin, i.e. in the direction of the part of the body, being possible, so that the apparatus can always remain positioned as close as possible to the part of the body.

DETAILED DESCRIPTION

Figure 1:
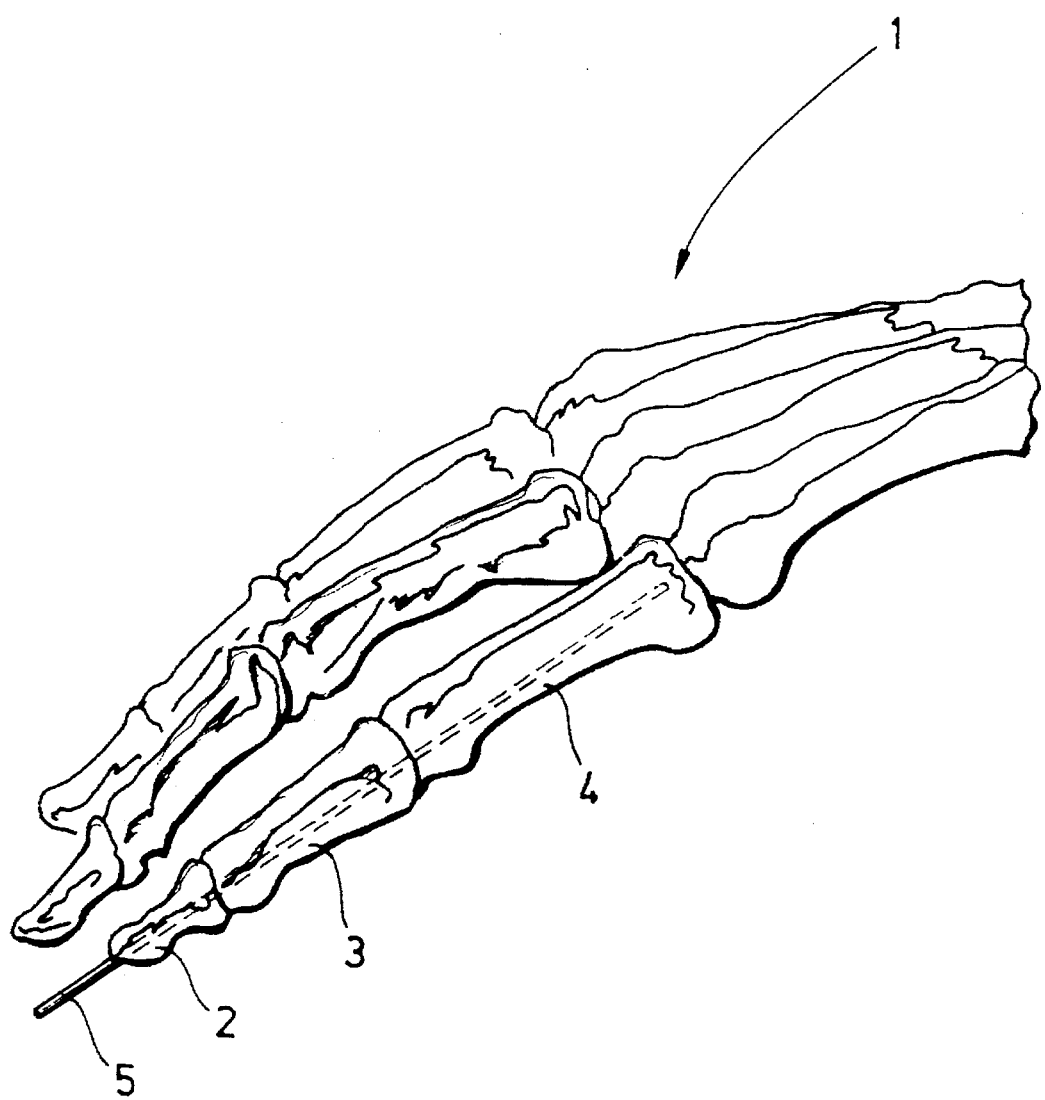

The invention will be explained in more detail below with reference to an illustrative embodiment shown in the drawing. In the drawing:

FIG. 1 shows, very diagrammatically, one use of pins inserted in a manner according to the invention in a patient's hand; and FIG. 2 shows a cross-section of an apparatus according to the invention for inserting pins by means of vibration.

In FIG. 1 the bone structure of a human hand is shown diagrammatically by 1. It is assumed that a break has occurred in some way between bones 2, 3 and 4 and has to be fixed. This is achieved by inserting a pin 5. As a consequence very limited movement is possible between bones 2, 3 and 4. A technique of this type is generally known in the prior art and in this case the pins are inserted by rotation.

In FIG. 2 the apparatus according to the invention is indicated in its entirety, in cross-section, by 10. This apparatus comprises a tube 11 provided with slots 9. A piston assembly 15 is incorporated in tube 11. This piston assembly comprises the piston sections 13 and 14, which are connected to one another by means of screws 20 and are put under tension with respect to one another by means of springs 19. The piston assembly 15 is fitted so that it is movable backwards and forwards between the position shown by the continuous line and the position shown by the dotted line. In the position shown by the dotted lane the piston assembly, and more particularly piston section 14, is to some extent clamped O-ring 30. The piston assembly is movable about guide tube 17. A transport cavity for wire 12, which is to be inserted, is provided in guide tube 17. The piston assembly can strike against stop 8. Tube 17 is confined by means of O-rings 18 between the stop 8 and the inlet end 7 of apparatus 10. The inlet end 7 is provided with a coupling 6, which is connected to a pulsed ear source. Stop 8 is connected to head 27, inside which the transport and clamping mechanism for the wire is located. This mechanism comprises a wedge surface 23, along which a slide piece 25, which is provided with rollers, is able to move backwards and forwards. Said rollers 22 engage on the other side with wire 12. By means of spring 24, slide piece 25 is moved to the right into the position shown in FIG. 2. As the piston assembly 15 moves to and fro, a percussion or vibratory movement is generated in the apparatus 10, as a result of which the wire is vibrated forwards. Orifice 26 of apparatus 10 must be positioned as close as possible to the part of the body to be provided with the pin. In order to compensate for machining tolerances with respect to the central positioning of guide tube 17 with respect to tube 11, the piston assembly 15 comprises, as described above, piston sections 13 and 14. With this arrangement the external diameter of piston section 13 is accurately adjusted to tube 11, so that no leakage can occur between the two. The internal diameter of piston section 14 is accurately adjusted to the external diameter of guide tube 17, so that, once again, no leakage can occur between the two. There is appreciable play between the bore in piston section 13 and guide tube 17 and between the outer circumferential surface of piston section 14 and the inner surface of tube 11. Because the piston sections adjoin one another in a sealing manner, a seal is provided between the guide tube and the interior of tube 11. The adjoinment is promoted by the presence of screws 20, which are fitted in threaded holes 21 and pretension a spring 19, which rests on piston section 14.

Compressed air is supplied in a vibratory manner via coupling 6. Said supply can be effected by any method disclosed in the prior art and as an example a construction with the aid of motor 40, transmission 41 and crank 42 is described. Crank 42, in turn, drives a piston 43, which is located in a cylinder 44. The frequency of the vibration can be determined by adjusting the speed of revolution of motor 40. The amplitude of each pulse of compressed air can be determined by adjusting the stroke on crank 42. It is obvious that such a vibration can also be generated by hydraulic or electrical means using other equipment.

The mass of piston assembly 15 should preferably be below 50 gram. If the weight is higher the risk that splintering will occur in the bone during insertion is not inconceivable. The mass is preferably about 20 gram, but tests have shown that results are also achieved with a weight of 12 gram. This is obviously dependent on the hardness of the cortex of the bone concerned and on the diameter and the tip of the wire used. The frequency used is preferably between 5 and 20 Hz. More particularly said frequency is about 15 Hz.

Although the invention has been described above with reference to a preferred embodiment, it must be understood that numerous modifications can be made thereto without going beyond the scope of the present Application for which rights are claimed in the appended claims. It is obvious that the apparatus will be completely modified if a different vibration medium is used.

We claim:

1. An apparatus for inserting a pin in osseous material by means of vibration comprising:

a distal section remote from the osseous material during use;

a proximal outer section located in a vicinity of the osseous material during use, said proximal outer section comprising pin clamping means immobile with respect to both said distal and proximal sections, said clamping means allowing free transport of the pin in a proximal-distal direction only;

pin vibration means located between said proximal section and said distal section;

a pin receiver comprising a cavity extending an entire length of said apparatus, said proximal and said distal sections being connected to one another and immobile with respect to one another to thereby keep said proximal section from vibrating with respect to said distal section during use.

2. An apparatus as claimed in claim 1, wherein the vibration means are provided with a means for controlling a vibration frequency.

3. The apparatus as claimed in claim 1, wherein the vibration means are provided with a means for controlling a vibration amplitude.

4. The apparatus as claimed in claim 1, wherein the vibration means operate at a frequency higher than 5 Hz.

5. The apparatus as claimed in claim 1, wherein the vibration means comprise a reciprocating percussion or vibration body, the mass of said body being below 50 grams, preferably about 20 grams.

6. The apparatus as claimed in claim 5, wherein the percussion body comprises a hollow piston assembly (15), a guide tube (17) for the pin (12) extending through said piston assembly.

7. The apparatus as claimed in claim 6, wherein the piston assembly comprises a first piston section (14) and a second piston section (13), said piston sections being movable relative to one another in a radial direction, one of said piston sections providing a seal with respect to a tube (11) surrounding said section and the other of the said piston sections providing a seal with respect to the guide tube (17) surrounded by said section.

\* \* \* \* \*